(12) United States Patent
Silva et al.

(10) Patent No.: US 6,392,079 B1
(45) Date of Patent: May 21, 2002

(54) METHOD AND APPARATUS FOR PREPARING MONOFUNCTIONAL AROMATIC CHLOROFORMATES SUITABLE FOR USE AS CHAINSTOPPING AGENTS

(75) Inventors: James Manio Silva, Clifton Park; David Michel Dardaris, Ballston Spa; Peter David Phelps, Schenectady, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/281,498

(22) Filed: Mar. 30, 1999

(51) Int. Cl.$^7$ .............................................. C07C 69/96
(52) U.S. Cl. ...................................... 558/282; 558/280
(58) Field of Search ......................................... 558/282

(56) References Cited

U.S. PATENT DOCUMENTS

| | | | |
|---|---|---|---|
| 4,864,011 A | | 9/1989 | Bussink et al. |
| 5,274,164 A | * | 12/1993 | Wetting et al. |
| 5,399,657 A | * | 3/1995 | Van Hout et al. |
| 5,426,170 A | | 6/1995 | Hirao et al. |

FOREIGN PATENT DOCUMENTS

| | | | |
|---|---|---|---|
| EP | 0207292 | | 1/1987 |
| EP | 0523686 | | 1/1993 |
| GB | 923192 | * | 4/1963 |

* cited by examiner

Primary Examiner—Gary Geist
Assistant Examiner—Leigh C. Maier

(57) ABSTRACT

A continuous process for the preparation of monofunctional aromatic chloroformates (MAC) having the structure (I)

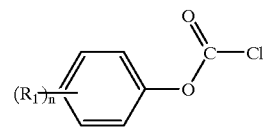

(I)

wherein n is an integer from 1 to 5, and $R_1$ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted, the method comprising the steps of a) introducing
1) an aqueous caustic solution;
2) a carbonyl chloride;
3) at least one monofunctional hydroxyaromatic compound; and
4) at least one inert organic solvent into a continuous reaction system; and b) effecting contact between 1), 2), 3) and 4) for a time and at conditions sufficient to produce a MAC of structure (I).

39 Claims, 2 Drawing Sheets

METHOD AND APPARATUS FOR PREPARING MONOFUNCTIONAL AROMATIC CHLOROFORMATES SUITABLE FOR USE AS CHAINSTOPPING AGENTS

FIELD OF THE INVENTION

This invention relates to a process and apparatus for the continuous preparation of monofunctional aromatic chloroformate products by an interfacial process. The monofunctional aromatic chloroformates are suitable for use as endcapping agents in polymer synthesis.

The present invention further relates to a process for preparation of a polycarbonate, in which the process for continuous preparation of monofunctional aromatic chloroformate products is coupled with an interfacial polycarbonate synthesis. The endcapping agents produced by the continuous process are introduced into the interfacial polycarbonate synthesis to obtain the desired polycarbonate product.

The present invention further relates to a method of controlling the variability of the molecular weight of polycarbonate produced in a series of batches. The method utilizes the process for the continuous preparation of monofunctional aromatic chloroformate products by an interfacial process.

BACKGROUND OF THE INVENTION

The introduction of monofunctional aromatic chloroformates into a polymer synthesis provides a means to control the molecular weight of the polymer to be formed. In general, the greater the quantity of endcapping agent introduced into a polymer synthesis, the lower the molecular weight of the polymer product. Monofunctional aromatic chloroformates are particularly suitable as endcapping agents in interfacial polycarbonate synthesis because they enable production of a polycarbonate in a single step phosgenation with a substantially lower level of diarycarbonate(s) (DAC) than products produced using a hydroxyaromatic endcap, such as p-cumyl phenol.

Diarylcarbonates have a low melting point, compared with the glass transition temperature of polycarbonate, and are therefore the last components to freeze during a polycarbonate molding operation. Therefore, polycarbonate with significant levels of DAC requires longer molding cycle times compared with polycarbonate that is substantially free of DAC. Further, because DAC can sublime, a polycarbonate containing diaryl carbonates can lead to undesirable effects, such as "plate out" in which the DAC from previous molding cycles condenses and deposits on the mold and leads to blemishes in subsequent moldings. The term "DAC" as used herein is understood to include also di(alkylphenyl carbonates) and di(arylphenyl)carbonates.

In making monofunctional aromatic chloroformates, it would be desirable to minimize production of by-product DAC. This would enable the monofunctional aromatic chloroformate to be used in a subsequent polymerization reaction without first being purified by such methods as distillation. In the following discussion, the term "MAC" or "MACs" refers to a monofunctional aromatic chloroformate compound or mixture of monofunctional aromatic chloroformate compounds.

Known process for the production of MACs by an interfacial process include the batchwise production of MACs, with subsequent storage for later use in polymerization.

U.S. Pat. No. 5,399,657 (Van Hout et al) discloses a method of preparing MAC in a batch process. A solution of phosgene in a solvent is introduced into a reactor, to which phosgene and a phenol compound are then added while maintaining the temperature at a value in the range of 3 to 5° C. The pH is maintained within a desired range by addition of an aqueous caustic solution. Excess phosgene is then depleted from the product by reaction with caustic. The production of MACs in U.S. Pat. No. 5,399,657 involve long batch times, typically in the range of 30 to 60 minutes.

U.S. Pat. No. 5,274,164 (Wettling et al) discloses a method of preparing aryl chloroformates by the reaction of phenols with phosgene in the presence of organic phosphorous compounds. The process requires long reaction times, and the addition of a catalyst, such as the organic phosphorous compounds, necessitates extra process steps to recover the catalyst from the product.

U.S. Pat. No. 4,864,011 (Bussink et al) discloses a method of preparation of an aromatic polycarbonate with a MAC endcapping agent. According to Bussink, the MAC is either present prior to phosgene addition, or is added at a single point in the batch polymerization reaction to produce polycarbonate with low DAC. This process, however, has several disadvantages. In order to deliver MAC to the polymerization reaction at a specific point during the polymerization, the MAC must be synthesized, purified, and stored. Further, delivery of a quantity of MAC at a specific point in the batch process usually requires an additional apparatus for storage and charging.

It would be desirable to develop a process whereby the MACs may be produced directly, without the need for purification, and in a continuous manner. It would be even more desirable to develop a continuous process whereby the MACs could be produced in an "on-demand" manner. This would permit direct coupling of the MAC process to a batch or continuous polymerization process, particularly a polycarbonate synthesis process. Such a directly coupled process would be desirable because it would avoid the risks associated with maintaining an inventory of MAC and phosgene-containing materials associated with MAC production.

An on-demand process for MAC synthesis would further provide a significant reduction in both phosgene exposure risks and cost of production compared with a batch process for MAC synthesis. None of the disclosures discussed above meet these criteria.

It would further be desirable to develop a process requiring shorter processing times to produce the MACs that may be coupled with a continuous or batch process for polycarbonate synthesis, respectively (without purification of the MAC) to produce a product having low DAC content and good quality.

It would also be desirable to develop a process in which excellent molecular weight control of a polycarbonate produced in an interfacial reaction is achieved. Molecular weight control is usually measured by the standard deviation of the molecular weight for a series of batches. Good molecular weight control, i.e. control of the variability of molecular weight of the polycarbonate produced in a reaction or series of reaction, is directly related to control of the molecular weight viscosity. Molecular weight determines molecular weight viscosity; therefore maintaining the molecular weight in a narrow range results in the maintenance of molecular weight viscosity in a narrow range. It is desirable to maintain the molecular weight viscosity in a narrow range to control processibility of the product. For example, narrow control of the molecular weight viscosity over a series of product batches would enable a molding machine that is processing polycarbonate from these batches to operate for extended periods of time without adjustment.

BRIEF SUMMARY OF THE INVENTION

The present invention solves these problems, and provides further surprising properties. These and further objects of the invention will be more readily appreciated when considering the following disclosure and appended claims.

In a first aspect, the invention relates to a continuous process for the preparation of monofunctional aromatic chloroformates (MAC) suitable for use as endcapping agents in polymer synthesis. In one embodiment, the invention relates to a continuous process for the preparation of monofunctional aromatic chloroformate (MAC) having the structure (I)

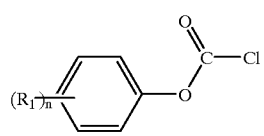

wherein n is an integer from 1 to 5, and $R_1$ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted, the method comprising the steps of a) introducing
 1) an aqueous caustic solution;
 2) a carbonyl chloride;
 3) at least one monofunctional hydroxyaromatic compound; and
 4) at least one inert organic solvent into a continuous reaction system; and b) effecting contact between 1), 2), 3) and 4) for a time and at conditions sufficient to produce a MAC of structure (I).

In another embodiment, the invention relates to a continuous process for the preparation of an MAC product having the structure (I), as defined above, comprising the steps of a) providing a reaction system comprising a reactor consisting essentially of a tubular reactor and a means for conveying fluids through the reactor; the tubular reactor having an input at the upstream end and an outlet at the downstream end;

b) introducing into the tubular reactor at the input of the upstream end a feed stream comprising an inert organic solvent and a monofunctional hydroxyaromatic compound;

c) introducing into the tubular reactor a carbonyl chloride;

d) introducing into the tubular reactor an aqueous caustic solution;

e) effecting contact between the carbonyl chloride, the monofunctional hydroxyaromatic compound and the aqueous caustic solution for a time period and at conditions sufficient to yield the MAC product.

In another embodiment, the invention relates to a tubular reactor system comprising a) a tubular reactor having an upstream end and a downstream end and at least one input and at least one output;

b) means to introduce carbonyl halide, aqueous caustic solution, monofunctional hydroxyaromatic compound and inert organic solvent to the reactor; the carbonyl halide, aqueous caustic solution, monofunctional hydroxyaromatic compound and inert organic solvent in the tubular reactor comprising a reaction mixture;

c) means to convey the reaction mixture through the tubular reactor, under turbulent flow conditions characterized by a Reynolds number of about 200 to about 100,000.

The invention further relates to MAC prepared by the aforementioned methods, reaction systems utilizing the method coupled with polycarbonate polymerization systems, and polycarbonates produced by these systems.

In a second aspect, the invention relates to a the preparation of polycarbonate products in a batch interfacial polymerization process coupled with the continuous process for the preparation of MAC products, and a method of controlling the variability of molecular weight in a series of product batches using this process.

In one embodiment, the invention relates method of preparing a polycarbonate comprising the steps of a) charging at least one dihydroxy compound, an inert organic solvent, water, caustic, carbonyl halide, and catalyst to a vessel, and maintaining the pH of the reaction mixture between about 4 and about 12; and b) within an interval of between 0 and about 90% of the total carbonyl halide addition to the vessel, activating a reaction system that produces monofunctional aromatic chloroformates (MAC) and introducing the MAC to the vessel within the interval of 0 to about 90% of the total carbonyl halide addition to the vessel; where the MAC reaction system is coupled with the vessel, and where means are provided for delivery of the MAC from the reaction system to the vessel.

The invention further relates to a method of controlling the variability of the molecular weight by repeating the process for the number of desired batches, with substantially the same amount of carbonyl halide, caustic and MAC and inert organic solvent. In a further embodiment, the invention relates to a method of preparing a poylcarbonate comprising the steps of:

a) charging a vessel with at least one dihydroxy compound, an inert organic solvent, water, and optionally caustic; thereby forming a reaction mixture;

b) after step a), simultaneously introducing a carbonyl halide and a caustic to the vessel containing the reaction mixture while maintaining the pH of the reaction mixture between about 4 and about 12;

c) within an interval of between 0 and about 90% of the total carbonyl halide addition to the vessel, activating a reaction system that produces monofunctional aromatic chloroformates (MAC) and introducing the MAC to the vessel within the interval of 0 to about 90% of the total carbonyl halide addition to the vessel; where the MAC reaction system is coupled with the vessel, and where means are provided for delivery of the MAC from the reaction system to the vessel.

The invention further relates to a method of controlling the variability of the molecular by repeating the process for the number of desired batches, with substantially the same amount of carbonyl halide, caustic and MAC.

DETAILED DESCRIPTION OF THE INVENTION

Figure 1:
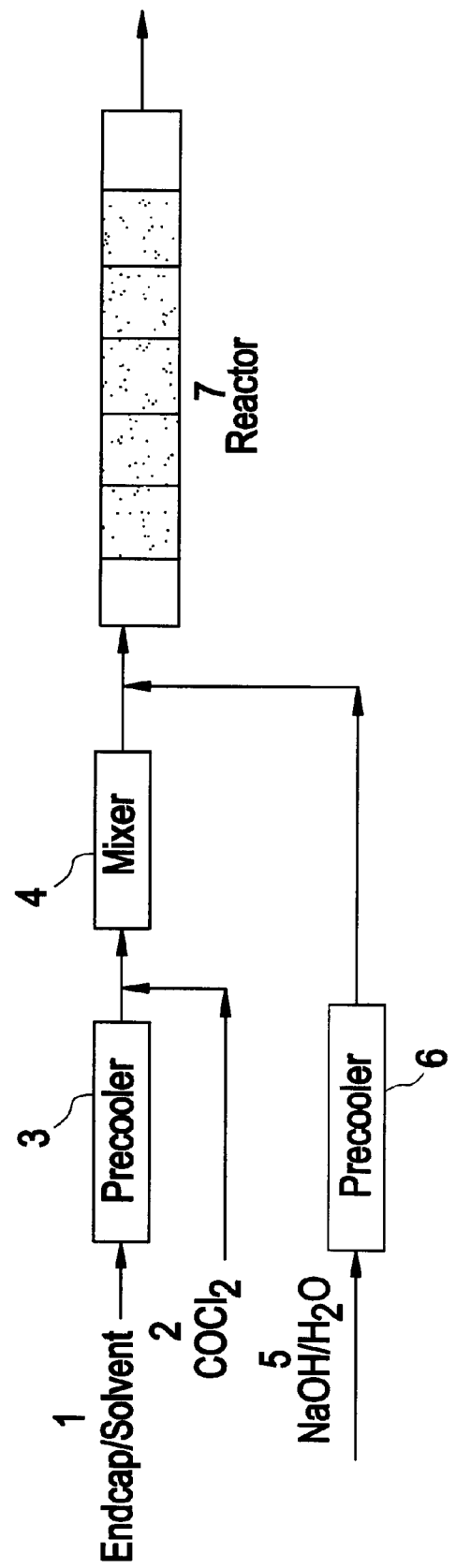
FIG. 1 is a schematic diagram of one embodiment of the invention to produce MAC by a continuous process.

The present invention may be understood more readily by reference to the following detailed description of the preferred embodiments of the invention and the examples included therein.

Before the present method and apparatus are disclosed and described, it is to be understood that this invention is not limited to specific systemic methods or to particular formulations, as such may, of course, vary. It is also to be understood that the terminology used herein is for the purpose of describing particular embodiments only and is not intended to be limiting.

In this specification and in the claims which follow, reference will be made to a number of terms which shall be defined to have the following meaning.

The singular forms "a", "an" and "the" include plural referents unless the context clearly dictates otherwise.

"Optional" or "optionally" mean that the subsequently described event or circumstance may or may not occur, and that the description includes instances where said event or circumstance occurs and instances where it does not.

"Molar flow rate" is in moles per minute, unless otherwise stated.

"Mixture average temperature" is defined as the temperature that a mixture of two or more combined streams achieves at equilibrium under adiabatic conditions, i.e., with no input or loss of heat.

An "on-demand" process, as used herein, enables production of the required amount of product during a specified time interval. An on-demand process is idle before and after the specified time interval. An on-demand process produces usable product from the moment it is started up through the time it is shut down. An on-demand process may also be operated continuously over an indefinite time interval, in order, for example, to feed a continuous polycarbonate synthesis process with MAC endcap.

A "monofunctional hydroxyaromatic" species, as contemplated herein, contains a single hydroxyl group or hydroxyl radical. In a MAC, this hydroxyl radical is replaced with a chloroformate group.

The term "polycarbonate" as used herein includes copolycarbonates, homopolycarbonates and (co) polyestercarbonates.

The terms "endcapping agent" and "chainstopping agent" are used interchangeably.

A "semi-batch" reactor receives an initial charge of materials, after which one or more reactants and optionally solvents are added to the reactor during the course of the reaction. Such reactors, however, are often referred to simply as "batch" reactors. The terms "batch" and "semi-batch" are used interchangeably throughout the rest of the specification.

Throughout this application, where publications are referenced, the disclosures of these publication are hereby incorporated by reference into this application in order to more fully describe the state of the art to which this invention pertains.

In one aspect, this invention concerns a continuous process for the production of MAC endcapping agents useful in polymer synthesis, in particular in polycarbonate synthesis.

In another aspect, this invention concerns a process for the production of polycarbonates in which a process for producing hydroxyaromatic haloformate endcapping agents is coupled with a reaction system for producing polycarbonate product.

I. Continuous Process for the Production of MACs

As mentioned, in a first aspect, the invention concerns the preparation of MAC products by an continuous process. The MAC products are suitable as endcapping agents in a polymer synthesis. "Reaction system" and "reactor" as used in section (I) of the specification refer to the continuous process for the production of MACs suitable for use as endcapping agents, and the equipment used to produce these products.

In semi-batch processes for the production of MAC products, the monofunctional hydroxyaromatic compound feed, a precursor to the MAC product, may be reacted away as it is fed to the reactor in order to maintain the concentration of the monofunctional hydroxyaromatic compound at a low level. In this way, it is possible to minimize the DAC formation reaction between the monofunctional hydroxyaromatic compound and the MAC product.

In contrast, in one embodiment of the continuous process of this invention, all of the monofunctional hydroxyaromatic compound is fed to a single input in a plug flow reactor system and reacts as it proceeds through the reactor. As the monofunctional hydroxyaromatic compound disappears by reaction, the MAC concentration increases. Therefore, there is a zone in the plug flow reactor where both the hydroxyaromatic and MAC concentrations are significant. It would be expected that within this reactor zone, the production rate of DAC would be rapid and that the reactor product would contain a high concentration of DAC. It was unexpectedly found, however, that the concentration of DAC in the product of the continuous process was extremely low, typically in the range of about 300–600 ppm (parts per million), relative to the weight of MAC in the product. This is particularly important for a process for making MACs that is directly coupled to a polycarbonate synthesis process In a continuous process according to the first aspect of this invention, it was also unexpectedly found that the monofunctional hydroxyaromatic feed material was virtually fully converted to MAC; only about 0.2 to about 4 weight percent of unconverted monofunctional hydroxyaromatic feed remained in the reactor product, relative to the weight of MAC product.

It was further unexpectedly found that the times for reaction to produce the MAC were very low. Typical reaction times in the batch process to produce MACs are in the range of about 30 minutes to 60 minutes. In one embodiment of the present invention, using a tubular reactor, the reaction of hydroxyaromatic compound to chloroformate was complete in about 1 to 5 seconds.

In batch reaction systems to produce MACs, it is important to maintain relatively low temperatures in order to avoid high levels of DAC formation, for instance, temperatures in the range of below about 10 to 15° C. It was unexpectedly found that low DAC product could be obtained in the continuous reactor system of the invention even when the reactor was operated adiabatically and allowed to achieve the boiling temperature of the solvent. In one embodiment, in which the solvent is methylene chloride, the continuous reaction system may achieve the boiling temperature of the solvent, about 40° C. while producing MAC with low levels of DAC.

More particularly, in a first aspect, the present invention relates to a continuous process for the interfacial preparation of endcapping agents useful in polymer synthesis, the endcapping agents having the formula (I):

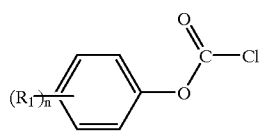

(I)

where n is an integer from 1 to 5, and R₁ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted. Endcapping agents produced by the method of the present invention include, but are not limited to, phenyl chloroformate, t-butyl phenyl chloroformate, p-cumyl chloroformate, chroman chloroformate, octyl phenyl or nonyl phenyl chloroformate, or a mixture thereof; more preferably phenyl chloroformate, p-cumyl chloroformate, or a mixture thereof; even more preferably p-cumyl phenylchloroformate. Compounds of structure (I) are herein referred to as MACs.

The process of the instant invention is conducted in a reaction system comprising a vessel or vessels in which the endcapping agent is produced in continuous manner by interfacial reaction. By "continuous" it is meant that reactants are introduced and products are withdrawn simultaneously from the reaction system. Further, the products may optionally be withdrawn in their entirety from the moment that the reactor system is started up through the moment that it is shut down, which has the added advantage of supplying MACs "on-demand" to another process, particularly an interfacial polycarbonate synthesis process. The reaction system may be coupled with a batch polymer synthesis with the MAC product introduced to the polymer synthesis reactor over a time interval, the reaction system may be coupled with a continuous polymer synthesis with the MAC product introduced into the continuous polymer synthesis reactor at a relatively constant rate indefinitely, or the MAC product may be stored in another vessel for later use.

The reaction system has an upstream inlet or input for introduction of feed and a downstream outlet, for recovery of product. Optionally, there may be inlets to the reaction system between the upstream inlet and the downstream outlet for introduction of feed.

The system allows for the continuous production by interfacial reaction of MACs, the product having a low level of DAC and unreacted monofunctional hydroxyaromatic compound. The continuous process may be conducted in any equipment arrangement in which a continuous reaction may be effected, including but not limited to a series of continuous stirred tank reactors (CSTRs), a tubular reactor or series of tubular reactors, one or more loop reactors in series and/or parallel, a network of CSTRs and tubular reactors, a column reactor having mixers in several stages, and an agitated column. The reaction system may comprise more than one stage, and cooling as well as introduction of additional reagents may be effected between stages.

An on-demand process, one embodiment of the invention, must satisfy much more rigorous requirements than simple continuous operation. For example, for an on-demand MAC synthesis process that is directly coupled to a batch polycarbonate synthesis reactor, the production rate of byproducts, e.g. DAC, during MAC synthesis must be low during the entire time from startup through shutdown. In contrast, many known continuous reaction processes do not have a low byproduct production rate during startup, or require lengthy times for startup. For example, chlorine synthesis is conducted continuously in diaphragm electrolytic cells, but several hours are required to start up a chlorine cell, and the by-product hydrogen level is elevated for much of the startup interval.

The continuous process to produce MACs, as described herein, may be optionally operated as an on-demand process.

Alternatively, the continuous process of MAC synthesis as disclosed herein may also be used to produce MACs for storage and subsequent use in, for example, a polycarbonate synthesis. If desired, the MAC may be isolated from the reaction product mixture using well known processes, such as distillation and decantation. The MAC product may be stored indefinitely as a solution in a solvent or as a neat liquid. It is preferable to keep the MAC solution or liquid cool and water-free. If there is any water present in the MAC liquid or solution, the MAC liquid or solution should be acidic.

It should be noted that the invention as disclosed also includes embodiments of continuous processes for MAC production that are not effective for "on-demand" operation. For example, in one embodiment of the invention, a continuous reaction process that comprises a tubular reactor with a short residence time (preferably 0.5 to 30 seconds) is followed by a surge tank with a long residence time (preferably greater than about 5 minutes). This process for MAC production is continuous but not on-demand. This process could be coupled to either a continuous or a batch polycarbonate synthesis process and would have the advantages described herein of MAC synthesis in a short residence time tubular reactor, but would not have the advantage of avoiding an inventory of MAC and residual phosgene. In contrast, a MAC production reactor that comprises a short residence time tubular reactor (without a downstream surge tank) that is directly coupled to a polycarbonate synthesis reactor may be operated as either a continuous or an on-demand reactor.

The products of the continuous process for MAC production may be added to a polycarbonate synthesis prior to or during a batch polycarbonate synthesis. In one embodiment of the invention, a reaction system in which the continuous process for MAC production is effected is coupled with a batch polymerization reactor, and the products of the MAC reactor are charged to the batch reactor before or during the polycarbonate synthesis.

The process conditions in the reaction system to produce the MACs may be varied, and generally any process conditions can be employed provided that the reaction between the carbonyl chloride and the monofunctional hydroxyaromatic compound occurs to produce the MAC product. The feed stream or streams entering the reaction system preferably have a mixture average feed temperature in the range of about −10° C. to about 40° C.; more preferably about 0° C. to about 25° C. The feed stream or streams contain the carbonyl chloride, inert organic solvent, aqueous caustic solution, and monofunctional hydroxyaromatic compound entering the reaction system.

The temperature of the mixture in the reaction system is preferably maintained below about 60° C., more preferably below about 50° C. The term "mixture" as used herein refers to the contents of the reaction system, including, but not limited to, the solvent or solvents, the reactants and the caustic. As the reaction is exothermic, the temperature of the reaction mixture increases as the reaction mixture is conveyed through the reaction system. The temperature at which any particular system is maintained depends on the particular solvents, reactants, cooling means, etc.

The reaction system may be cooled or operated adiabatically. Suitable cooling means include a cooling jacket, a pre-cooler heat exchanger, a heat exchanger in a recirculation loop, a heat exchanger between sections of a multiple reactor system, or a reflux condenser. The reaction vessel or vessels may be cooled, or heat may be removed between the reaction vessels, if the system comprises more than one stage. For simplicity in both design and operation, it is preferable to operate the system adiabatically. In order to achieve adiabatic reactor conditions, the reaction vessel or vessels may be insulated according to typical industrial practice.

Prior to introduction into the reaction system, the feed stream or streams may optionally be mixed by suitable mixing means, including but not limited to, an in-line or static mixer, and an orifice mixer. As mentioned "feed stream" or "feed streams" as defined herein refers to the components entering the reaction system, and may include one or more streams entering the reaction system. A mixing zone may be established before the reaction system, the reaction system may comprise a mixing zone, or both.

While in the reaction system, the mixture is preferably agitated at an intensity at least sufficient to prevent segregation of the aqueous and organic phases. If segregation occurs, the conversion of the reactants to the product will be reduced. The agitation of the aqueous and organic phase should be regulated such that phosgene is not wasted by increasing its hydrolysis rate, which may occur at excessively intense mixing.

In a tubular reactor, one embodiment of the invention, the mixing intensity is often characterized by a tube Reynolds number, defined as:

$$N_{Re} = \frac{Dv\rho}{\mu}$$

where
D=tube diameter (cm)
v=solution velocity through tube (cm/sec)
ρ=solution density (gm/cc)
μ=solution viscosity (gm/cm-sec)

It is preferable to maintain the tube Reynolds number in the range of about 200 to about 100,000, more preferably in the range of about 200 to about 20,000.

The mixture in the reaction system may be agitated by mechanical mixing means, or alternatively, static mixing elements may be placed in the reaction vessel. Static mixing technology is discussed in "Advances in Static Mixing Technology", M. Mutsakis, F. Streiff, and G. Schneider, Chemical Engineering Progress, July, 1986.

The reaction to produce MAC requires an alkali metal base and/or an alkaline-earth metal base herein referred to as a caustic compound. The caustic compound is preferably introduced as an aqueous caustic solution comprising the caustic compound. The aqueous caustic solution preferably comprises potassium hydroxide, sodium hydroxide and mixtures thereof, even more preferably sodium hydroxide. The aqueous caustic solution preferably has a strength of about 10 to about 50 weight percent, preferably between about 15 to about 40 weight percent.

The aqueous caustic solution is preferably introduced into the continuous reaction system in a separate stream from the stream containing the monofunctional hydroxyaromatic compound and the stream containing the carbonyl halide. In one embodiment, the aqueous caustic solution stream is introduced at the upstream input of the reaction system. Alternatively, the aqueous caustic solution stream may be introduced at any point or input in the reaction system which allows the reaction in the system of the carbonyl halide and the monofunctional hydroxyaromatic compound to form the MAC. The aqueous caustic solution stream may optionally be split into two or more streams which may have the same or different molar flow rates. These streams may be introduced at different points in the reaction system. It is preferable to introduce the aqueous caustic solution stream at the upstream inlet of the reaction system.

In one embodiment of the invention, the reaction system further comprises a first precooler to establish an input temperature for the monofunctional hydroxyaromatic compound and inert organic solvent, a second precooler to establish an input temperature for the aqueous caustic solution, and a mixer that is coupled to the first precooler and the carbonyl halide feed stream. The monofunctional hydroxyaromatic compound is preferably dissolved in the solvent in this embodiment. The aqueous caustic solution is fed to the second precooler. The cooled aqueous caustic solution and the exit stream from the mixer are then fed to the reactor, preferably a tubular reactor.

In the continuous process described herein, it is common for the reactor product to contain some unreacted carbonyl chloride and some unreacted caustic. As caustic is preferably introduced in a separate stream and caustic is needed for the conversion of the monofunctional hydroxyaromatic compound to the MAC, it is possible to control the extent of the reaction, or conversion, in a given section of the reactor by adjusting the proportion of caustic solution added to that section.

Under substantially adiabatic reaction conditions, the amount of caustic introduced into the reactor section relative to the amount of hydroxyaromatic compound and other feed species determines the extent of temperature increase in that section. The temperature sensitivity of the reaction selectivity towards MAC synthesis and away from DAC formation is a key factor which is considered in determining the amount of caustic to be added per stage, the number of stages, and the need for interstage cooling, particularly under adiabatic conditions.

In the present invention, the carbonyl chloride and caustic are introduced into the reaction system at flow rates which are based on molar ratios to the monofunctional hydroxyaromatic compound feed rate. Thus, carbonyl halide hydrolysis and the formation of undesired side products, such as DAC, and residual hydroxyaromatic compound are minimized by employing a reaction procedure in which primary attention is given to maintaining the molar flow ratios of the caustic and carbonyl halide to the monofunctional hydroxyaromatic compound feed rate, with only secondary attention being directed to pH. These ratios may vary depending on the desired quality of the product solution, production rate requirements, and the operating parameters of the reaction system.

The ratio of the molar flow rates of the carbonyl chloride, such as phosgene, to the monofunctional hydroxyaromatic compound into the reaction system is preferably from about 1.05:1 to about 10:1, more preferably from about 1.5:1 to about 5:1, even more preferably from about 2:1 to about 4:1. The ratio of the molar flow rates of the caustic (as equivalents of NaOH) to the monofunctional hydroxyaromatic compound in the reaction system is preferably from about 1.1:1 to about 3:1, more preferably from about 1.2:1 to about 2:1, even more preferably from about 1.3:1 to about 1.7:1.

The components may be fed to the reaction system in separate streams, or alternatively, some components may be combined prior to introduction into the reaction system. For example, the carbonyl chloride and the monofunctional hydroxyaromatic compound may each be introduced in one or more feed streams, at an input at the upstream end of the reaction system or at an input at any point in the reaction system. The overall molar ratios, however, must be maintained in the reaction system, i.e. between the input and output of the reaction system.

In one embodiment, the carbonyl chloride is mixed with the inert organic solvent prior to introduction into the reaction system as a homogeneous solution. In another embodiment, the carbonyl chloride is mixed with the inert organic solvent into which has been dissolved at least one monofunctional hydroxyaromatic compound, whereupon the mixture is fed as a homogeneous solution. The carbonyl chloride may alternatively be introduced into the reaction system in the form of a gas. The aqueous caustic solution is preferably fed to the reaction system in a separate stream from the input stream or streams containing the carbonyl chloride and the monofunctional hydroxyaromatic compound.

If the reaction system comprises more than one stage, feed may be introduced into the reaction system between stages. Feed may include one or more of the following: aqueous caustic solution, inert organic solvent, carbonyl chloride, and monofunctional hydroxyaromatic compound. In one embodiment, the invention is a tubular reactor which comprises from one to four stages.

The monofunctional hydroxyaromatic compound may be introduced into the reaction system as a solution, as a solid, as a melt, or a mixture thereof. The weight of the monofunctional hydroxyaromatic compound input to the reaction system, relative to the weight of the inert organic solvent input to the reaction system is from about 0.5:99.5 to about 20:80. The monofunctional hydroxyaromatic compound may be included in whole or in part in the inert organic solvent stream introduced into the reaction system. In one embodiment, the monofunctional hydroxyaromatic compound is dissolved in the inert organic solvent and the stream is fed into an input of the reaction system at the upstream end. If dissolved in the inert organic solvent, it is preferable that the monofunctional hydroxyaromatic compound comprises from about 1 to about 20% by weight of the solution. Optionally, carbonyl chloride, such as phosgene, may be dissolved in this stream. Alternatively, the inert organic solvent and the hydroxyaromatic compound may be introduced in separate streams at the input of the reaction system at the upstream end, or each stream may be divided into two or more streams and introduced at input points along the reaction system.

The residence time of the reaction mixture in the reaction system is a function of volumetric flow rate through the reaction system. If the reaction system is a tubular reactor, for instance, the length and diameter of the reactor may be varied to achieve a desired residence time and thereby achieve an optimum yield of the desired MAC product.

Design consideration that are common to plug flow reactors are described by Levenspiel in *Chemical Reaction Engineering,* John Wiley and Sons, 1962. Preferably, the length to diameter ratio of the tubular reactor is at least about 10, and more preferably at least about 20.

In the present invention it was surprisingly found that the residence time in the reactor is not critical. It was also surprisingly found that extra residence time in the reactor will not degrade the product. In general, the reaction occurs at a fast rate; the preferred residence time in the reactor may vary from about 0.5 seconds to about 30 seconds per stage, more preferably from about 1 to about 10 seconds per stage.

It is preferable to maintain the reaction system at substantially amine free conditions. By "substantially amine free" it is meant that the flow rate weighted average of the amine levels, including but not limited to triethylamines, in all feed streams be maintained at less than 50 parts per million (ppm), preferably below about 10 ppm, even more preferably below about 5 ppm. The presence of amines in the reaction system leads to undesirable side products, such as DAC. Optionally the feed stream(s) entering the reaction system may be purified by acid extraction; any of the feed streams may be purified by passing the desired stream over an adsorbent bed to remove free amines. In addition, it is also preferable to avoid other condensation catalysts besides amines, including but not limited to quaternary ammonium salts and quaternary phosphonium salts, and organophosphorous catalysts.

Optionally, the MAC reaction product may be treated with further processing steps. Although the MAC reaction product from the process of this invention has sufficiently low DAC levels to be used without further purification for polymer production, such as a polycarbonate, optionally, the product solution may be further purified by fractional distillation prior to introduction into a polymerization, i.e. a polycarbonate synthesis.

In one embodiment, the process of the instant invention is conducted in a tubular reactor system as illustrated in FIG. 1. The tubular reactor may be situated in any manner; however it is preferred that the tubular reactor is horizontally displaced. Feed stream 1, containing monofunctional hydroxyaromatic compound and solvent are fed to precooler 3. The product of precooler 3 and feed stream 2 containing carbonyl chloride, such as phosgene, are fed to mixer 4. A separate stream of an aqueous caustic solution 5 is fed into precooler 6. The effluents from mixer 4 and precooler 6 are then fed into the tubular reactor 7. The diagram of reactor 7 includes mixing elements in the reactor. Optionally, tubular reactor 7 may be insulated. The effluent from tubular reactor 7, containing the MAC product (product stream) may be further processed, or it may be directed into a polymer synthesis reactor, for example a polycarbonate synthesis reactor.

The process as shown in FIG. 1 may be operated continuously or in an on-demand manner, depending on the intended use of the MAC product. If the process is operated in an on-demand manner, it may be started while a batch polycarbonate synthesis is being conducted in a separate vessel. The MAC product may be introduced into the polycarbonate synthesis reactor during the phosgenation step of the batch polycarbonate synthesis, and then stopped prior to completion of the polycarbonate batch. The MAC product stream may be delivered directly into the polycarbonate synthesis reactor without the need for further purification.

Figure 2:
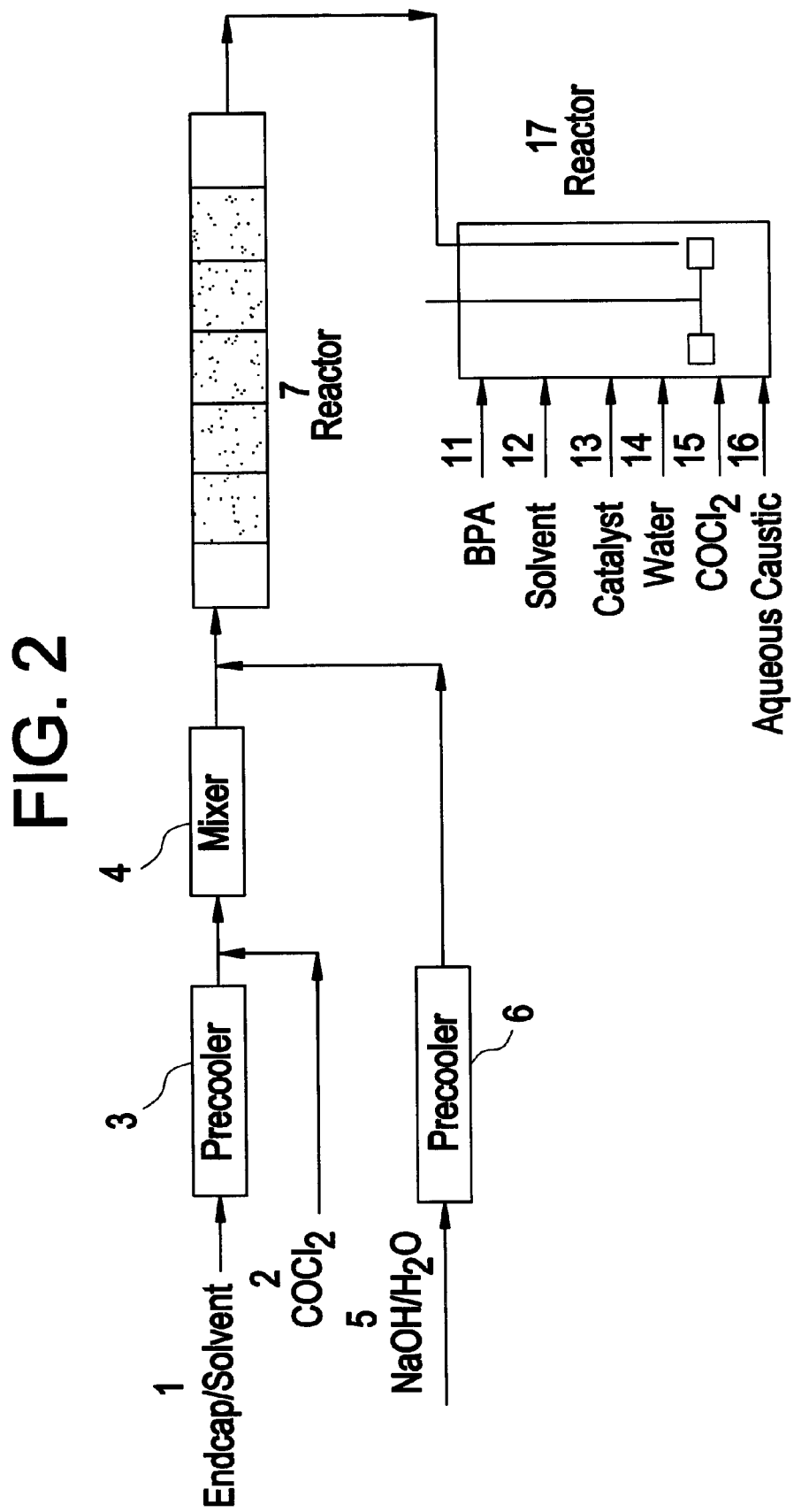
FIG. 2 is a schematic diagram of one embodiment of the invention to produce polycarbonate, in which a continuous process to product MAC is coupled with a polycarbonate synthesis reaction.

As shown in FIG. 2, a tubular reactor system may be connected in series to a polycarbonate synthesis reactor 17. One embodiment of the batch polymerization is discussed in section 11 of the specification. The polycarbonate synthesis reactor may be operated either continuously or in a batch mode. In the continuous operating mode, the product from the reactor 7 is continuously introduced into the polycarbonate synthesis reactor 17. In a batch operating mode, the polycarbonate reactor may be charged with monomer, for example bisphenol-A (BPA) 11, solvent 12, catalyst 13, water 14, phosgene 15, and an aqueous caustic solution 16 as disclosed in U.S. Pat. No. 4,864,011, incorporated herein by reference. In the polymerization disclosed in U.S. Pat. No. 4,864,011, a MAC chainstopper is added to the polycarbonate synthesis reaction after 20 to 80 percent of the carbonyl halide that is to be added in total has been supplied to the reactor. Each example in U.S. Pat. No. 4,864,011 shows the entire charge of chloroformate being added at a single point in the batch polymerization process.

The following discussion sets forth the reactants, including caustic, and solvents which are suitable for use in the preparation of the MAC products suitable for use as end-capping agents. The particular components described are for illustrative purposes only, and the provided lists are not intended to be exhaustive.

Suitable monofunctional hydroxyaromatic compounds which may be used in the process of the present invention to prepare MAC are represented by the general formula (II):

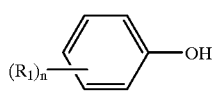

II where n is an integer from 1 to 5, and wherein $R_1$ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted. It is preferred that n is equal to 1 and that $R_1$ is present in the para position.

Monofunctional hydroxyaromatic compounds as defined in formula (II) include, but are not limited to, phenol, p-tert-butylphenol, o-cresol, m-cresol, p-cresol, o-ethylphenol, p-ethylphenol, p-cumylphenol, chroman, p-octylphenol, p-nonylphenol, a-napthol, α-napthol and mixtures thereof. Preferred monofunctional hydroxyaromatic compounds are phenol, t-butyl phenol, p-cumyl phenol, chroman, and mixtures thereof; p-cumyl phenol is more preferred.

Suitable carbonyl halides for use in the present process, include, but are not limited to carbonyl chlorides, such as phosgene, carbonyl bromide, carbonyl iodide, carbonyl fluoride and mixtures thereof. Other carbonyl chlorides including diphosgene and triphosgene are also suitable. Phosgene is the preferred carbonyl halide. The carbonyl halide may be introduced into the reaction system in the form of a gas or a liquid, or it may be dissolved in any feed stream except the caustic feed stream before the introduction of the feed stream into the reaction system. It is therefore possible to prepare other haloformates, such as bromoformates, etc. by the process of the invention. Chloroformates are the most preferred.

Suitable inert organic solvents for use in the process of the present invention include any inert organic solvent which is substantially insoluble in water and inert to the process conditions. The inert organic solvent should also be a liquid under the reaction conditions and should not react with the carbonyl halide, the hydroxyaromatic compound or the caustic. It is desirable that the MAC product be soluble in the solvent. Suitable inert organic solvents include, but are not limited to aliphatic hydrocarbons such as pentane, hexane, cyclohexane, and heptane; aromatic hydrocarbons such as toluene, xylene; substituted aromatic hydrocarbons, such as chlorobenzene, dichlorobenzene, and nitrobenezene; chlorinated aliphatic hydrocarbons such as chloroform and methylene chloride, and mixtures of any of the aforementioned solvents. The aforementioned solvents may also be mixed with ethers, including but not limited to tetrahydrofuran. Chlorinated aliphatic hydrocarbons are preferred, in particular methylene chloride.

The reaction to produce the MAC requires an alkali metal base and/or an alkaline-earth metal base, herein referred to as a caustic. The caustic compound is preferably introduced as an aqueous solution comprising the alkali metal base and/or alkaline-earth metal base.

Suitable alkali metal compounds which may be used as a caustic in the reaction system include, but are not limited to, sodium hydroxide, potassium hydroxide, lithium hydroxide, sodium hydrogen carbonate, potassium hydrogen carbonate, lithium hydrogen carbonate, sodium carbonate, potassium carbonate, lithium carbonate and mixtures thereof.

Suitable alkaline-earth metal compounds which may be used as a caustic in the reaction system include, but are not limited to, calcium hydroxide, barium hydroxide, magnesium hydroxide, strontium hydroxide, calcium hydrogen carbonate, barium hydrogen carbonate, magnesium hydrogen carbonate, strontium hydrogen carbonate, calcium carbonate, barium carbonate, magnesium carbonate, strontium carbonate and mixtures thereof.

The strength of the aqueous caustic solution may be varied, however it is preferable that the caustic compound comprise from about 10 wt % to about 50 wt % of the aqueous caustic solution, preferably between about 15 to about 40 wt %. The most preferred caustic is sodium hydroxide, and the aqueous caustic solution preferably comprises from about 15wt % to about 40 wt % sodium hydroxide.

II. Batch Process for the Production of Polycarbonate by Interfacial Polymerization In a second aspect, the present invention concerns the preparation of polycarbonate products in a batch interfacial polymerization process coupled with the continuous process for the preparation of MAC products as set forth in section I of the specification, and a method of controlling the variability of molecular weight in a series of product batches using this process.

Polycarbonates which may be prepared by the method of this invention typically comprise structural units of the formula

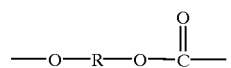

III wherein at least about 60% of the total number of R groups are aromatic organic radicals and the balance thereof are aliphatic, alicyclic or aromatic radicals. Preferably, each R is an aromatic organic radical and more preferably a radical of the formula

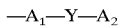        IV wherein each $A_1$ and $A_2$ is a is a monocyclic divalent aryl radical and Y is a bridging radical in which one or two carbonate atoms separate $A_1$ and $A_2$. Such radicals may be derived from dihydroxyaromatic compounds of the formulas OH—R—OH and OH—$A_1$—Y—$A_2$—OH, or their corresponding derivatives. $A_1$ and $A_2$ include but are not limited to unsubstituted phenylene, preferably p-phenylene or substituted derivatives thereof. The bridging radical Y is most often a hydrocarbon group and preferably a saturated group, such as methylene, cyclohexylidene or isopropylidene. Isopropylidene is the more preferred. Thus, the more preferred polycarbonates are those comprising residues of 2,2-bis(4- hydroxyphenyl)propane, also known as "bisphenol A". In one embodiment, the polycarbonate is a homopolymer of bisphenol A.

(Co)polyestercarbonates may also be prepared by the method of this invention. The polyestercarbonate may comprise residues of aliphatic or aromatic diacids. The corresponding derivatives of aliphatic or aromatic diacids, such as the corresponding dichlorides, may also be utilized in the polymerization.

Polyfunctional compounds may also be introduced into the reaction to produce, for example, branched polycarbonates.

Polycarbonates, including aromatic polycarbonates, are typically produced interfacially by the reaction of a carbonyl halide, such as phosgene, and a bisphenol, such as bisphenol A, in the presence of a phenolic endcapping agent. Known methods include the addition of the phenolic endcapping agent at the beginning of the interfacial reaction which leads to the production of undesirable diarylcarbonates (DAC). In contrast, in a preferred batch polycarbonate synthesis process as described herein, the MAC is prepared in an on-demand manner and added over a finite interval during the batch polymerization.

It was unexpectedly found that when the batch polymerization reaction to produce polycarbonates, as defined in section II of the specification, was coupled with the continuous process for the production of MAC as described in section I of the specification, the molecular weight of the polycarbonate product over a series of batches showed less variability than when previously known methods for endcap addition, such as the addition of molten or solid endcap, in particular p-cumyl phenol, were used It was also unexpectedly discovered that, when the batch polymerization reaction to produce polycarbonate was coupled with the continuous process for the production of MAC as set forth in Section I of the specification, by adding the MAC endcap over an interval during the batch polycarbonate synthesis, that the final DAC level in the polycarbonate product was lower than the level previously obtained by adding MAC to the polycarbonate synthesis at a single point in the batch polycarbonate synthesis process, as was disclosed by Bussink et al in U.S. Pat. No. 4,864,011.

In one embodiment, the combined MAC and batch polycarbonate synthesis comprises the steps of 1) charging at least one dihydroxy compound, an inert organic solvent, water, caustic, carbonyl halide, and catalyst to a vessel, and maintaining the pH of the reaction mixture between about 4 and about 12 during charging; and 2) within an interval of between 0 and about 90% of the total carbonyl halide addition to the vessel, activating a reaction system that produces monofunctional aromatic chloroformates (MAC) and introducing the MAC to the vessel within the interval of 0 to about 90% of the total carbonyl halide addition to the vessel; where the MAC reaction system is coupled with the vessel, and where means are provided for delivery of the MAC from the reaction system to the vessel.

In a further embodiment, the combined MAC and batch polycarbonate process of this invention preferably comprises the steps of 1) charging a batch polymerization reactor with at least one dihydroxy compound, solvent, and water, and optionally caustic 2) simultaneously charging carbonyl halide and caustic to the reactor, while maintaining a pH of the reaction in a specified range, 3) charging the batch polymerization reactor with the MAC reactor products during a specified interval of the batch polymerization process, and 4) recovering the polycarbonate polymer from the batch polymerization reactor.

The first step of the process is referred to herein as the batch formulation. In this step, a batch interfacial polycarbonate reaction is generally initiated by charging a vessel with a mixture of solvent, one or more monomers, for example bisphenol A, and optionally a comonomer such as 2,2-bis(3,5-dibromo-4-hydroxyphenyl)propane), water, and catalyst, such as triethylamine. The relative amounts of solvent and monomer are established in order to achieve a desired final polycarbonate concentration in the organic phase preferably in the range of from about 5 wt % to about 25 wt %, more preferably in the range of from about 15 wt % to about 25 wt %, accounting for solvent added during the formulation as well as solvent added during the MAC synthesis and addition. The amount of water added during the batch formulation is established so that the final concentration of byproduct alkali halide, for example sodium chloride, is preferably in the range of from about 10 wt % to saturation, which is about 26 wt % for sodium chloride, and more preferably from about 15 wt % to about 25 wt %. These ranges are commonly used in industry and are described in U.S. Pat. No. 3,173,891, herein incorporated by reference.

During the batch phosgenation of the polycarbonate reaction, alkali metal base and/or alkaline earth metal base is added to maintain the reaction pH preferably in the range of about 4 to about 12, more preferably in the range of about 7 to about 11 for polyester carbonate reactions, and more preferably in the range of about 9 to about 11 for Bisphenol A polycarbonate synthesis reactions. The types and concentrations of bases described in Section I of the specification are also usable in the polycarbonate synthesis process.

During the batch formulation, the MAC synthesis reactor is idle, if the MAC synthesis reactor is operated as an on-demand process. It is preferable to operate the reaction system as an on demand process. The MAC synthesis reactor may start either at or about the time phosgene addition begins or at a specified time after the carbonyl halide, such as phosgene)addition starts for the batch polymerization reactor. When a predetermined condition in the batch polymerization has been achieved, for example, a specific percent of the total carbonyl halide addition, the MAC synthesis reactor is started and the MAC reactor products are delivered to the batch polymerization reaction over a predetermined interval. Again, this interval is usually specified in terms of a percentage of the total carbonyl halide target to the polymerization reactor.

Preferably, the MAC product mixture prepared by the on demand process is added during the interval of 0 and about 90 percent of the phosgene addition to the batch polycarbonate synthesis. More preferably, the MAC product mixture from the on demand process is added during the interval of about 10 and about 80 percent of the phosgene addition to the batch polycarbonate synthesis. Even more preferably, the MAC product mixture from the on-demand process is added during the interval of 10 and about 60 percent of the phosgene addition to the batch polycarbonate synthesis. Alternatively, if the MAC synthesis process is simply continuous, and not on demand, the batch polymerization reactor may be fed with MAC product mixture over the same intervals noted above, but the MAC product mixture is fed from a storage vessel, such as a surge tank, rather than directly from the MAC synthesis reactor.

The carbonyl halide and caustic addition rates for the polycarbonate synthesis reaction may vary during the course of the polymerization reaction. Although it is preferable to add both the phosgene and caustic to the polymerization reaction during the interval that MAC is being generated and added to the polymerization reactor in order to minimize the batch reaction cycle time, it is within the scope of this invention to suspend or reduce phosgene and/or caustic addition to the polymerization reactor during part or all of the interval during which MAC is fed to the polymerization reactor.

The total amount of MAC added to the batch polycarbonate synthesis is in the range of about 1 mole percent to about 20 mole percent, based on the number of moles of difunctional monomer in the polymerization, and preferably in the range of about 1 mole percent to about 7 mole percent, based on the number of moles of difunctional monomer in the polymerization. The rate of addition of the MAC product mixture to the polycarbonate synthesis may vary over the course of addition to the batch polymerization reaction, but it is preferable to add the MAC mixture at a substantially constant rate to the polycarbonate synthesis.

It is preferable to predetermine a reaction endpoint for the batch interfacial polycarbonate synthesis reaction. The predetermined reaction endpoint for a batch interfacial polycarbonate synthesis reaction may be, for example, attainment of a specific total amount of phosgene or caustic addition to the polycarbonate synthesis reaction. Alternatively, the properties of the reactor contents may be measured intermittently or continuously, for example the weight average molecular weight may be monitored by laser light scattering. When the measured property achieves a desired level, this signifies the reaction endpoint. At this point, the carbonyl halide addition is stopped; caustic addition may continue until a final reaction pH is achieved.

The polycarbonate from the batch polymerization process may be recovered according to practices well known in the art for solution polymerizations. Several well-known techniques such as antisolvent precipitation are described in *Chemistry and Physics of Polycarbonates*, H. Schnell and *Polycarbonates*, by W. F. Christopher and D. W. Fox.

The transport of the MAC from the continuous reaction system used to produce the MAC to the polycarbonate synthesis reaction (batch polymerization reaction) may be accomplished by any suitable delivery system, for example, a pipe between the two reaction systems. The delivery time between the MAC reaction system and the polycarbonate synthesis depends on the length and diameter of the delivery system; it is preferable that the delivery time is in the range of about 1 to about 30 seconds. Preferably, the MAC reaction system is placed as close as possible to the batch reactor to minimize the potential of phosgene exposure risk.

It should be noted that the MAC purity is unaffected by delays in additional piping between the MAC synthesis reactor and the polycarbonate synthesis reactor. The reaction product from the continuous process for the production of MAC as described in section I of the specification contains not only MAC, but also unreacted carbonyl halide and caustic, as well as solvent and aqueous alkali halide solution. Therefore, if any hydrolysis of the MAC product back to monofunctional hydroxyaromatic compound occurs within the tubular reactor or while the MAC product mixture is being conducted to the polycarbonate polymerization reactor, the residual carbonyl halide and caustic will tend to reconvert hydrolyzed product to the desired MAC.

The following discussion sets forth reactants and solvents which are suitable for use in the preparation of the polycarbonates by a batch or continuous interfacial polymerization process. The solvents, caustic, carbonyl halides, and monofunctional hydroxyaromatic compounds which may be used in the production of the MAC as discussed in section (I) of the specification may also be used in the batch process for the preparation of polycarbonate. The particular reactants and catalysts as described are for illustrative purposes only, and the provided lists are not intended to be exhaustive.

Suitable carbonyl halides for use in the polycarbonate synthesis process, include, but are not limited to carbonyl chloride, carbonyl bromide, carbonyl iodide, carbonyl fluoride and mixtures thereof. Diphosgene and triphosgene are also suitable carbonyl halides. Phosgene is the preferred carbonyl halide.

It is to be understood that, although "chloroformates" are the preferred endcapping agent produced and utilized according to the method of this invention as described in sections I and II of the specification, other haloformates may be prepared, and have the general formula described in formula V, below, in which X represents fluorine, bromine, chlorine or iodine. The corresponding carbonyl halide, as discussed above would be utilized in production of the haloformate endcapping agent.

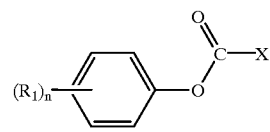

V

Suitable organic solvents for use in the polycarbonate synthesis include any organic solvent which is substantially insoluble in water and inert to the process conditions. The organic solvent should also be a liquid under the reaction conditions and should not react with the carbonyl halide, or the caustic. Suitable organic solvents include, but are not limited to aliphatic hydrocarbons such as pentane, hexane, cyclohexane, and heptane; aromatic hydrocarbons such as toluene, xylene; substituted aromatic hydrocarbons, such as chlorobenzene, dichlorobenzene, and nitrobenezene; chlorinated aliphatic hydrocarbons such as chloroform and methylene chloride, and mixtures of any of the aforementioned solvents. The aforementioned solvents may also be mixed with ethers, including but not limited to tetrahydrofuran. Chlorinated aliphatic hydrocarbons are preferred, in particular methylene chloride.

Suitable bisphenols or diphenols which may be used in the polymerization of polycarbonate include, but are not limited to, resorcinol, 4-bromoresourcinol, hydroquinone, 4,4'-dihydroxybiphenyl, 1,6-dihydroxynapthalene, bis(4-hydroxyphenyl)methane, bis(4-hydroxyphenyl)diphenylmethane, bis(4-hydroxyphenyl)-1-napthylmethane, 1,1-bis(4-hydroxyphenyl)ethane, 1,2-bis(4-hydroxyphenyl)ethane, 1,1-bis(4-hydroxyphenyl)phenylethane, 2,2-bis(4-hydroxyphenyl)propane ("bisphenol A"), 2-(4-hydroxyphenyl)-2-)3-hydroxyphenyl)propane, 2,2-bis(4-hydroxyphenyl)butane, 1,1-bis(4-hydroxyphenyl)isobutane,
1,1-bis(4-hydroxyphenyl)cyclohexane,
trans-2,3-bis(4-hydroxyphenyl)-2-butene,
2,2-bis(4-hydroxyphenyl)adamantane,
α,α'-bis(4-hydroxyphenyl)toluene,
bis(4-hydroxyphenyl)acetonitrile,
2,2-bis(3-methyl-4-hydroxyphenyl)propane,
2,2-bis(3-ethyl-4-hydroxyphenyl)propane,
2,2-bis(3-n-propyl-4-hydroxyphenyl)propane,
2,2-bis(3-sec-butyl-4-hydroxyphenyl)propane,
2,2-bis(3-t-butyl-4-hydroxyphenyl)propane,
2,2-bis(3-cyclohexyl-4-hydroxyphenyl)propane,
2,2-bis(3-allyl-4-hydroxyphenyl)propane,
2,2-bis(3-methoxy-4-hydroxyphenyl)propane,
2,2-bis(3,5-dimethyl-4-hydroxyphenyl)propane,
2,2-bis(2,3,5,6-tetramethyl-4-hydroxyphenyl)propane,
2,2-bis(3,5-dichloro-4-hydroxyphenyl)propane,
2,2-bis(3,5-dibromo-4-hydroxyphenyl)propane,
2,2-bis(2,6-dibromo-3,5-dimethyl-4-hydroxyphenyl)propane,
α,α-bis(4-hydroxyphenyl)toluene,
α,α,α',α'-tetramethyl-α,α'-bis(4-hydroxyphenyl)p-xylene,
2,2-bis(4-hydroxyphenyl)hexafluoropropane,
1,1-dichloro-2,2-bis(4-hydroxyphenyl)ethylene,
1,1-dibromo-2,2-bis(4-hydroxyphenyl)ethylene,
1,1-dichloro-2,2-bis(5-phenoxy-4-hydroxyphenyl)ethylene,
4,4'-dihydroxybenzophenone,
3,3-bis(4-hydroxyphenyl)-2-butanone,
1,6-bis(4-hydroxyphenyl)-1,6-hexanedione,
ethylene glycol bis(4-hydroxyphenyl)ether,
bis(4-hydroxyphenyl)ether,
bis(4-hydroxyphenyl)sulfide,
bis(4-hydroxyphenyl)sulfoxide,
bis(4-hydroxyphenyl)sulfone,
bis(3,5-dimethyl-4-hydroxyphenyl)sulfone,
9,9-bis(4-hydroxyphenyl)fluorene,
2,7-dihydroxypyrene,
6,6'-dihydroxy-3,3,3',3'-tetramethylspiro(bis)indane ("spirobiindane bisphenol"),
3,3-bis(4-hydroxyphenyl)phthalide,
2,6-dihydroxydibenzo-p-dioxin,
2,6-dihydroxythianthrene,
2,7-dihydroxyphenoxathiin,
2,7-dihydroxy-9,10-methylphenazine,
3,6-dihydroxydibenzofuran,
3,6-dihydroxydibenzothiophene,
2,7-dihydroxycarbazole,
4,4-bis(4-hydroxyphenyl)heptane,
2,2-bis(4-hydroxyphenyl)hexane,
and other halogenated or alkylated derivatives. It is also possible to use mixtures of mono- and/or bischloroformates of the desired bisphenol or mono- and/or bis-chloroformate oligomeric carbonate mixtures of the desired bisphenol. 2,2-bis(4-hydroxyphenyl)propane (or bisphenol A) is the preferable bisphenol. The corresponding derivates of the diphenols may also be used.

Suitable polyfunctional compounds used in the polymerization of branched polycarbonate include, but are not limited to,
1,1,1-tris(4-hydroxyphenyl)ethane,
4-[4-[1,1-bis(4-hydroxyphenyl)-ethyl]-dimethylbennzyl],
trimellitic anhydride,
trimellitic acid, or their acid chloride derivatives.
Suitable dicarboxylic acids or dicarboxylic dichlorides which may be used with bisphenols in the polymerization of polyester carbonates include, but are not limited to,
1,10-decane dicarboxylic acid,
1,12-dodecane dicarboxylic acid,
terephthalic acid,
isophthalic acid,
terephthaloyl dichloride, and isophthaloyl dichloride.

The polycarbonate synthesis may be conducted in the presence of a catalyst, for example a tertiary amine and/or a phase transfer catalyst, such as a tetraalkylammonium salt. Suitable tertiary amine catalysts include, but are not limited to triethylamine, tripropylamine, and tributylamine. Phase transfer catalysts include but are not limited to tetrabutylammonium bromide and methyl tributylammonium bromide. The amine catalyst level may be in the range of from about 0.25 to about 10 mole percent based on dihydroxy compound. The phase transfer catalyst may be in the range of zero to about 2 mole percent based on the dihydroxy compound. The catalyst mixture may be charged to the reactor prior to addition of the carbonyl halide addition or may be programmed into the batch or continuous polymerization reactor during addition of the carbonyl halide.

EXAMPLES

The following examples are set forth to provide those of ordinary skill in the are with a complete description of how the compositions of matter and methods claimed herein are made and evaluated, and are not intended to limit the scope of what the inventors regard as their invention. Efforts have been made to insure accuracy with respect to numbers (e.g., amounts, temperature, etc.) but some errors and deviations should be accounted for. Unless indicated otherwise, parts are by weight, temperature is in ° C.

Example 1

A tubular reactor was constructed of 0.25 inch outer diameter 316 stainless steel tubing and SWAGELOK® fittings, manufactured by Swagelok Company, and was packed with static mixing elements. The overall length of the reactor was 16.5 inches. The reactor was insulated with woven fabric insulating material. The reactor was fed from two feedstreams: a solution of phosgene and p-Cumyl Phenol (PCP) in methylene chloride, and NaOH/water. Each feed solution was pumped independently to the reactor via a pre-cooling coil immersed in a water bath that was held at 4° C. The details of the reaction are shown in the table below. The product composition is reported as parts by weight of the organic phase product.

For example wt % PCP=100(wt PCP)/(wt PCP+wt PCF+wt DAC)

Feed (1):
4.5 gm/min p-cumyl phenol
92.1 gm/min methylene chloride
4.2 gm/min $COCl_2$ Feed (2):
  25 wt % NaOH Solution

| Expt | mole NaOH/mole PCP | Product DAC (ppm) | Product PCP (wt %) |
|---|---|---|---|
| A | 1.0 | 633 | 0.46–3.32 |
| B | 1.2 | 421 | 0.248 |
| C | 1.5 | 336 | 0.228 |

The balance of the aromatic product of these reactions was p-cumyl phenyl chloroformate, the desired product. These results show that very low levels of DAC and essentially complete PCP conversion are achieved with the process of this invention.

Example 2

A tubular reactor was constructed as in example 1 except that it comprised two 7 inch sections that contained mixing elements followed by a 50 foot section of unpacked tubing. The entire reactor was insulated with woven fabric. This reactor was fed with feeds 1 and 2 as shown below. The feeds were cooled to 4° C. prior to being introduced into the reactor. The reaction was sampled after the first and second 7 inch mixing section and after the 50 foot unpacked section.
Feed (1):
  4.5 gm/min p-cumyl phenol
  92.1 gm/min methylene chloride
  4.2 gm/min COCl$_2$
Feed (2):
  25 wt % NaOH Solution (1.5 mole NaOH/mole PCP)
The product composition is shown below. The balance of the aromatic product was p-cumyl phenyl chloroformate.

| Sample Point | ppm DAC | wt % PCP |
|---|---|---|
| 7" | 430 | 0.7 |
| 14" | 410 | 1.2 |
| 14" + 50 Feet | 430 | 0.6 |

This example shows that the product is not further converted to DAC upon additional residence time in the tubular reactor or in downstream piping.

Example 3

Example 2 was repeated with 5 ppm triethylamine in the methylene chloride feed solution. The results are given in the table below.

| Sample Point | ppm DAC | wt % PCP |
|---|---|---|
| 7" | 530 | 0.7 |
| 14" | — | 0.6 |
| 14" + 50 Feet | 600 | 0.5 |

This shows that the reaction product is sensitive to the presence of low levels of triethylamine.

Example 4

Example 2 was repeated using only the two packed sections and with the following feed composition. The precooling bath temperature was adjusted to values between 20 and 35° C. The product composition was measured at the end of the second mixing zone.
Feed (1):
  4.5 gm/min p-cumyl phenol
  92.1 gm/min methylene chloride
  5.2 gm/min COCl$_2$
Feed (2):
  24 wt % NaOH Solution (1.5 mole NaOH/mole PCP)

| Bath Temp C | ppm DAC | wt % PCP |
|---|---|---|
| 20 | 325 | 0.7 |
| 25 | 420 | 0.5 |
| 30 | 460 | 0.8 |
| 35 | 470 | 0.6 |

This example shows that the reaction may be run over a wide range of temperature without introducing high levels of DAC in the product.

Examples (Polycarbonate)

The following examples relate to the preparation of a polycarbonate by a batch interfacial polymerization process coupled with the continuous process for the preparation of MAC, used as an endcapping agent.

Examples 5–10

A chloroformate synthesis reactor was constructed of TEFLON lined pipe and packed with static mixing elements. The reactor was 1 inch inside diameter by 5 feet in length. The reactor was fed with three feedstreams: a solution 4 wt % p-cumylphenol (PCP) in methylene chloride, phosgene gas, and a 25 wt % solution of NaOH in water. The PCP solution was pumped through a heat exchanger to the cool it to the desired feed temperature before sending it to the chloroformate synthesis reactor.

An agitated polycarbonate synthesis reactor was equipped with inlets to charge phosgene and NaOH, a pH probe to measure and control the pH of the reaction, and a reflux condenser. This reactor was charged with BPA (200 pounds), water (56 gallons), methylene chloride (93 gallons) and triethylamine (450 ml). Phosgene (250 pounds/hour) was added to the polycarbonate synthesis reactor and an aqueous caustic solution (50 wt % NaOH) was added to maintain a pH of 9–11. While maintaining the phosgene and NaOH flows to the polycarbonate reactor, the MAC synthesis reactor was flushed with methylene chloride into the polycarbonate reactor. Phosgene and NaOH/water where then added to the methylene chloride flush at predetermined rates described in the table below. After the flows of the phosgene and NaOH/water were established, the methylene chloride flush was stopped and a cooled solution of 4 wt % PCP in methylene chloride (257 pounds) was pumped to the chloroformate synthesis reactor while maintaining the phosgene and NaOH/water flows to the chloroformate synthesis reactor. After the addition of the 4 wt % PCP methylene chloride, the chloroformate synthesis reactor was flushed briefly with methylene chloride and the flows of phosgene and NaOH/water were stopped. The phosgene flow was continued to the polycarbonate reactor until a total of 87 pounds was achieved. During this time, the pH was maintained at 9–11 by addition of 50% NaOH. After the phosgene was shut off, the methylene chloride phase of the polycarbonate reaction was sampled. The resulting polymer analyzed for di-p-cumylphenylcarbonate (a DAC) and the results are reported below.

The following definitions are used in the table below.
Start Time=Time in minutes after the start of phosgenation when the MAC reactor was started.
Feed Time=Time interval during which the 4 wt % PCP in methylene chloride solution is fed to the chloroformate synthesis reactor.
wt % NaOH=The weight percent NaOH in water added to the MAC synthesis reactor.
$R_{NaOH}$=Mole of NaOH per mole of PCP fed to chloroformate synthesis reactor
$R_{phos}$=Mole of phosgene per mole of PCP fed to chloroformate synthesis reactor

| EX | Start time | Feed Time | Feed Temp | wt % NaOH | $R_{NaOH}$ | $R_{phos}$ | ppm DAC |
|---|---|---|---|---|---|---|---|
| 5 | 4 | 7 | 55 | 20 | 1.5 | 3.5 | 174 |
| 6 | 4 | 5 | 45 | 25 | 1.5 | 2.8 | 74 |
| 7 | 2 | 5 | 55 | 25 | 1.5 | 2.8 | 82 |
| 8 | 2 | 7 | 55 | 30 | 1.5 | 3.5 | 102 |
| 9 | 4 | 5 | 55 | 30 | 1.5 | 2.8 | 75 |
| 10 | 2 | 5 | 55 | 0 | 0 | 0 | 2100 |

The above table shows that the polymer product DAC level is below about 200 ppm over a broad range of MAC synthesis reactor operating conditions. For comparison, Example 10 shows that the polymer product DAC level was significantly higher when neither phosgene nor caustic were added to the chloroformate synthesis reactor. This represents the polymer product DAC level that occurs when PCP rather than p-cumyl phenyl chloroformate is added to the polycarbonate synthesis reactor over an interval during polycarbonate synthesis.

Example 11 (Polycarbonate)

The combined chloroformate synthesis reactor and polycarbonate synthesis reactor were operated as in Example 5 (POLYCARBONATE) to make a series of six polycarbonate batches with the same MAC endcap level. The product weight average molecular weight (Mw) was measured for each batch. We were surprised to find that the molecular weight was quite consistent, as shown in the table below. For this data set, the standard deviation of the molecular weight is only 52 Mw units, which is comparable to the variability of the molecular weight measurement. When the conventional endcap addition technique is used, the molecular weight variability is about 150 Mw units.

| Batch | DAC ppm | Mw |
|---|---|---|
| a | 220 | 17,600 |
| b | 150 | 17,620 |
| c | 220 | 17,600 |
| d | 180 | 17,575 |
| e | 125 | 17,500 |
| f | 180 | 17,500 |

Comparative Example 1

Bussink et al (U.S. Pat. No. 4,864,011) report DAC levels for polycarbonate polymerizations in which all the MAC was added at a single point in the phosgenation reaction. The MAC (as phenyl chloroformate) endcap level for the reactions reported by Bussink was 5.6 mole percent of the BPA repeat units. In the examples of this invention, substantially the same mole percent (5.5) of MAC as p-cumyl phenyl chloroformate was used. The table below compares the molar concentration of DAC between the Bussink results and the process of this invention. The process of this invention has a significantly lower molar level of DAC in the polycarbonate product than the lowest level reported by Bussink et al.

| Process | MAC Addition Interval (% of Total Phosgene to Polycarbonate Reactor) | Product DAC level micromole DAC/ mole Repeat Unit |
|---|---|---|
| Bussink et al | 0 (single point) | 388 |
| " | 20 (single point) | 157 |
| " | 30 (single point) | 128 |
| " | 40 (single point) | 139 |
| This Invention | 10–40 Interval | 42–124 (range of DAC levels in Examples 10–11) |

This invention has been described in detail with particular reference to preferred embodiments thereof, but it will be understood that variations and modifications can be effected within the spirit and scope of the invention.

What is claimed is:

1. A continuous process for the preparation of monofunctional aromatic chloroformates (MAC) having the structure (I)

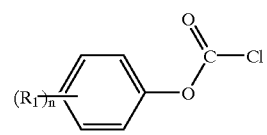

wherein n is an integer from 1 to 5, and $R_1$ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted, the method comprising the steps of a) introducing
   1) an aqueous caustic solution;
   2) a carbonyl chloride;
   3) at least one monofunctional hydroxyaromatic compound; and
   4) at least one inert organic solvent into a continuous reaction system; and b) effecting contact between 1), 2), 3) and 4) for a time and at conditions sufficient to produce a product comprising a MAC of structure (I) wherein the product comprises a maximum DAC content of from about 300 ppm to about 600 ppm relative to the weight of MAC in the product.

2. The method of claim 1, wherein the continuous process is effected in a tubular reactor having from one to four stages.

3. The method of claim 1, wherein the continuous process is effected in a tubular reactor having one stage.

4. The method of claim 1, wherein the continuous reaction system contains less than 50 ppm of triethylamine.

5. The method of claim 1, wherein in the continuous reaction system, the contact between the aqueous caustic solution, the carbonyl chloride, the monofunctional hydroxyaromatic compound and the inert organic solvent is conducted in the absence of organo-phosphorous catalysts.

6. The method of claim 1, wherein the monofunctional hydroxyaromatic compound is selected from the group consisting of phenol, p-tert-butylphenol, o-cresol, m-cresol, p-cresol, o-ethylphenol, p-ethylphenol, p-cumylphenol, chroman, p-octylphenol, p-nonylphenol, α-napthol, β-napthol and a mixture thereof.

7. The method of claim 1, wherein the monofunctional hydroxyaromatic compound is selected from the group consisting of phenol, t-butyl phenol, p-cumyl phenol, chroman, and a mixture thereof.

8. The method of claim 1, wherein the monofunctional hydroxyaromatic compound is p-cumyl phenol.

9. The method of claim 1, wherein the continuous process is operated as an on-demand process and is coupled to a batch polycarbonate synthesis.

10. The method of claim 2, wherein the residence time in the continuous reaction system is from about 0.5 seconds to about 30 seconds per stage.

11. The method of claim 2, wherein the residence time in the continuous reaction system is from about 0.5 to about 10 seconds per stage.

12. The method of claim 3, wherein the residence time in the continuous reaction system is about 0.5 seconds to about 30 seconds.

13. The method of claim 3, wherein the residence time in the continuous reaction system is from about 0.5 to about 10 seconds.

14. The method of claim 1, wherein the carbonyl chloride and the monofunctional hydroxyaromatic compound are introduced into the reaction system at a first molar flow rate ratio of from about 1.05:1 to about 10:1; and the caustic and the monofunctional hydroxyaromatic compound are introduced into the reaction system at a second molar flow rate ratio of from about 1.1:1 to about 3:1.

15. The method of claim 1, wherein the weight of the monofunctional hydroxyaromatic compound relative to the weight of inert organic solvent is from about 0.5:99.5 to about 20:80.

16. The method of claim 1, wherein the strength of the aqueous caustic solution is about 10 to about 50 weight percent.

17. The method of claim 1, wherein the contents of the reaction system are maintained at a temperature of below about 60° C.

18. The method of claim 1, wherein the carbonyl chloride is phosgene.

19. The method of claim 1, wherein the inert organic solvent is selected form the group consisting of pentane, hexane, cyclohexane, heptane; toluene, xylene; chlorobenzene, dichlorobenzene,nitrobenezene; chloroform; methylene chloride, and mixtures thereof.

20. The method of claim 1, wherein the inert organic solvent is methylene chloride.

21. The method of claim 1, wherein steps a) and b) are conducted simultaneously.

22. The method of claim 1, wherein the process is operated adiabatically.

23. A continuous process for the preparation of monofunctional aromatic chloroformates (MAC) having the structure (I)

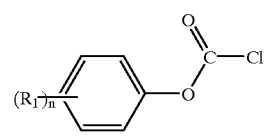

wherein n is an integer from 1 to 5, and $R_1$ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted, the method comprising the steps of:

a) providing a reaction system comprising a reactor consisting essentially of a tubular reactor and a means for conveying fluids through the reactor; the tubular reactor having an input at the upstream end and an outlet at the downstream end;

b) introducing into the tubular reactor at the input of the upstream end a feed stream comprising an inert organic solvent and a monofunctional hydroxyaromatic compound;

c) introducing into the tubular reactor a carbonyl chloride;

d) introducing into the tubular reactor an aqueous caustic solution;

e) effecting contact between the carbonyl chloride, the monofunctional hydroxyaromatic compound and the aqueous caustic solution for a time period and at conditions sufficient to to produce a product comprising the MAC of structure (I) wherein the product comprises a maximum DAC content of from about 300 ppm to about 600 ppm relative to the weight of MAC in the product.

24. The method of claim 22, wherein the reaction system further comprises a first precooler, a second precooler, and a mixer that is coupled with the first precooler, wherein the monofunctional hydroxyaromatic compound is dissolved in the inert organic solvent and fed to the first precooler and upon exiting the first precooler is fed to the mixer, and wherein the aqueous caustic solution is fed to the second precooler; the streams exiting the first and second precoolers being fed to the tubular reactor.

25. The method of claim 23, wherein the carbonyl chloride is introduced at the upstream end of the tubular reactor.

26. The method of claim 23, wherein the aqueous caustic solution is introduced at the upstream end of the tubular reactor.

27. The method of claim 23, wherein the carbonyl chloride is dissolved in the feed stream that is introduced at the upstream end of the tubular reactor.

28. The method of claim 23, wherein the carbonyl chloride is phosgene.

29. The method of claim 23, wherein steps b) through e) are conducted simultaneously.

30. The method of claim 23, wherein the carbonyl chloride and the monofunctional hydroxyaromatic compound are introduced into the tubular reactor at a first molar flow rate ratio of from about 1.05:1 to about 10:1; and the caustic and the monofunctional hydroxyaromatic compound are introduced into the tubular reactor at a second molar flow rate ratio of from about 1.1:1 to about 3:1.

31. The method of claim 23, wherein in the reaction system, the contact between the aqueous caustic solution, the carbonyl chloride, the monofunctional hydroxyaromatic compound and the inert organic solvent is conducted in the absence of additional catalysts.

32. The method of claim 23, wherein the continuous reaction system contains less than 50 ppm triethylamine.

33. The method of claim 23, wherein in the reaction system, the contact between the aqueous caustic solution, the carbonyl chloride, the monofunctional hydroxyaromatic compound and the inert organic solvent is conducted in the absence of organo-phosphorous catalysts.

34. The method of claim 23, wherein the process is operated adiabatically.

35. The method of claim 23, wherein the process is operated in such a manner that the Reynolds number is from 200 to 100,000.

36. A continuous process for the preparation of paracumyl phenyl chloroformate comprising the steps of:
   a) providing a reaction system comprising a reactor consisting essentially of a tubular reactor and a means for conveying fluids through the reactor; the tubular reactor having an input at the upstream end and an outlet at the downstream end;
   b) introducing into the tubular reactor at the input of the upstream end a feed stream comprising methylene chloride and paracumyl phenol;
   c) introducing phosgene into the tubular reactor;
   d) introducing an aqueous caustic solution into the tubular reactor;
   e) effecting contact between the phosgene, the paracumyl phenol and the aqueous caustic solution for a time period and at conditions sufficient to to produce a product comprising paracumyl phenol chloroformate, and wherein the product comprises a maximum DAC content of from about 300 ppm to about 600 ppm relative to the weight of paracumyl phenol chloroformate in the product.

37. The method of claim 36, further comprising the step of f) recovering a product stream comprising paracumyl phenyl chloroformate from the outlet end of the tubular reactor.

38. A continuous process for the preparation of monofunctional aromatic chloroformates (MAC) having the structure V
   wherein n is an integer from 1 to 5, and $R_1$ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted, and X represents bromine, fluorine, iodine or chlorine, the method comprising the steps of
   a) introducing
      1) an aqueous caustic solution;
      2) a carbonyl halide;
      3) at least one monofunctional hydroxyaromatic compound; and
      4) at least one inert organic solvent into a continuous reaction system; and
   b) effecting contact between 1), 2), 3) and 4) for a time and at conditions sufficient to produce a product comprising a MAC of structure V wherein the product comprises a maximum DAC content of from about 300 ppm to about 600 ppm relative to the weight of MAC in the product.

39. A continuous process for the preparation of monofunctional aromatic chloroformates (MAC) having the structure (I)

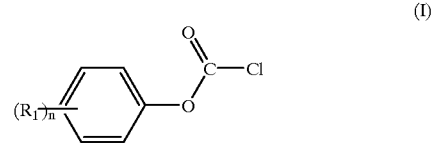

wherein n is an integer from 1 to 5, and $R_1$ represents hydrogen, a branched or unbranched alkyl group having from 1–15 carbon atoms, an aryl group which may be substituted or unsubstituted, a cycloaliphatic group which may be substituted or unsubstituted, or an arylalkyl group which may be substituted or unsubstituted, the method comprising the steps of
   a) introducing
      1) an aqueous caustic solution;
      2) a carbonyl chloride;
      3) at least one monofunctional hydroxyaromatic compound; and
      4) at least one inert organic solvent into a continuous reaction system; and
   b) effecting contact between 1), 2), 3) and 4) for a time and at conditions sufficient to produce a MAC of structure (I) wherein the process is operated as an on demand process and is coupled to a batch polycarbonate synthesis.

* * * * *